(12) United States Patent
Timmins et al.

(10) Patent No.: US 8,394,839 B2
(45) Date of Patent: Mar. 12, 2013

(54) RATIONALLY IMPROVED ISONIAZID AND ETHIONAMIDE DERIVATIVES AND ACTIVITY THROUGH SELECTIVE ISOTOPIC SUBSTITUTION

(75) Inventors: Graham Timmins, Albuquerque, NM (US); Vojo P Deretic, Placitas, NM (US)

(73) Assignees: STC.UNM, Albuquerque, NM (US); The John Hopkins University, Baltimore, MD (US)

( * ) Notice: Subject to any disclaimer, the term of this patent is extended or adjusted under 35 U.S.C. 154(b) by 18 days.

(21) Appl. No.: 12/674,188

(22) PCT Filed: Aug. 20, 2008

(86) PCT No.: PCT/US2008/009909
§ 371 (c)(1),
(2), (4) Date: May 13, 2011

(87) PCT Pub. No.: WO2009/025820
PCT Pub. Date: Feb. 26, 2009

(65) Prior Publication Data
US 2011/0218220 A1 Sep. 8, 2011

Related U.S. Application Data

(60) Provisional application No. 60/965,600, filed on Aug. 21, 2007, provisional application No. 61/127,150, filed on May 9, 2008.

(51) Int. Cl.
*A61K 31/4409* (2006.01)
*C07D 213/86* (2006.01)
(52) U.S. Cl. ........................................ 514/354; 546/324

(58) Field of Classification Search .................. 546/324; 514/354
See application file for complete search history.

(56) References Cited

FOREIGN PATENT DOCUMENTS
WO 2008156471 A1 12/2008

OTHER PUBLICATIONS

Jamart-Gregoire, 1665, Synthesis, vol. 3, p. 269-270.*
Timmins GS et al., Nitric Oxide Generated from Isoniazid Activation by KatG: Source of Nitric Oxide and Activity against Mycobacterium tuberculosis. Antimicrobial Agents and Chemotherapy 2004, 48(8):3006-3009.
Brosse N. et al., Synthesis of N-(protected)aminophthalimides: appliciation to the synthesis of singly labelled isoniazid. J. Chem. Soc., Perkin Trans. 1, 1998:3685-3688.
Debarber AE et al., Ethionamide activation and sensitivity in multidrug-resistant Mycobacterium tuberculosis. Proc. Natl. Acad. Sci., USA 2000, 97(17):9677-9682.
Wang F et al., Mechanism of thioamide drug action against tuberculosis and leprosy. J Exp Med 2007, 204:73-78.
Schantl J et al., Synthesis (Stuttgart) 1980 9:694-695. (translation into English language only).
Feely WE et al., Cyanation of Amine Oxide Salts. A New Synthesis of Cyanopyridines. J. Am. Chem. Soc. 1959, 81:4004-4007.
Nguyen M et al., A Fast and Efficient Metal-Mediated Oxidation of Isoniazid and Identification of Isoniazid-NAD(H) Adducts. Chembiochem 2001, 2:877-833.

* cited by examiner

*Primary Examiner* — Golam M M Shameem
*Assistant Examiner* — Karen Cheng
(74) *Attorney, Agent, or Firm* — Henry D. Coleman; R. Neil Sudol; William J. Sapone

(57) ABSTRACT

The present invention relates to the use of isotopically labeled derivatives of isoniazid, ethionamide and related compounds as effective therapy for the treatment of mycobacterial diseases, including *Mycobacterium tuberculosis*.

26 Claims, 3 Drawing Sheets

1. Great similarity between Ethionamide and Isoniazid Activation

RATIONALLY IMPROVED ISONIAZID AND ETHIONAMIDE DERIVATIVES AND ACTIVITY THROUGH SELECTIVE ISOTOPIC SUBSTITUTION

RELATED APPLICATIONS

This application claims the benefit of priority of provisional application Ser. No. U.S. 61/127,150, filed May 9, 2008 and U.S. 60/965,600, filed Aug. 21, 2007, each of which applications is incorporated by reference in its entirety herein.

GOVERNMENT SUPPORT

This application was made with government support under Grant No. R21 AI063486-02 and Grant No. AI042999 awarded by the National Institutes of Health. Consequently, the Government retains certain rights in the invention.

FIELD OF THE INVENTION

The present invention relates to the use of isotopically labeled derivatives of isoniazid, ethionamide and related compounds as effective therapy for the treatment of mycobacterial diseases, including *Mycobacterium tuberculosis*.

BACKGROUND OF THE INVENTION

Recently, the present inventors have shown that isoniazid specifically substituted in the acyl position with $^{13}C$ greatly increase isoniazid activity, through enhanced formation of INH-NAD and NADP adducts after its activation by the bacterial enzyme KatG, with these adducts being the species that are highly toxic to mycobacteria. It is believed that this is due to kinetic isotope effects on several steps of the pathway, although effects in the reversibility of acyl radical addition to the NAD, perhaps play the major role. It has been shown that another major TB drug, ethionamide (and its related compound prothionamide), undergoes almost identical activation and adduct formation chemistries (Wang, et al J Exp Med 204 73-8 2007). This chemistry is shown in FIG. 1 attached, with a highly reversible initial adduct being formed.

BRIEF DESCRIPTION OF THE INVENTION

The present invention relates to novel compounds according to the chemical structure:

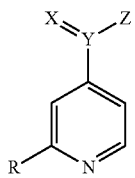

Where

X is an oxygen or a sulfur atom selected from the group consisting of $^{16}O$, $^{17}O$, $^{18}O$, $^{32}S$, $^{33}S$ and $^{34}S$;

Y is a carbon atom selected from the group consisting of $^{12}C$ and $^{13}C$;

Z is a $NH_2$ group or a $NHNH_2$ group, which group is optionally isotopically labeled with at least one $^{15}N$ atom, preferably two $^{15}N$ atoms in the case of a $NHNH_2$ group;

R is H or a $C_1$-$C_3$ alkyl group, preferably H or an ethyl group, with the proviso that R is H and Z is an optionally isotopically labeled $NHNH_2$ group when X is an oxygen atom and R is a $C_1$-$C_3$ alkyl group, preferably an ethyl group and Z is an optionally isotopically labeled $NH_2$ group when X is a sulfur atom;

Wherein at least one of X, Y and Z is isotopically labeled, or a pharmaceutically acceptable salt thereof.

Figure 1:
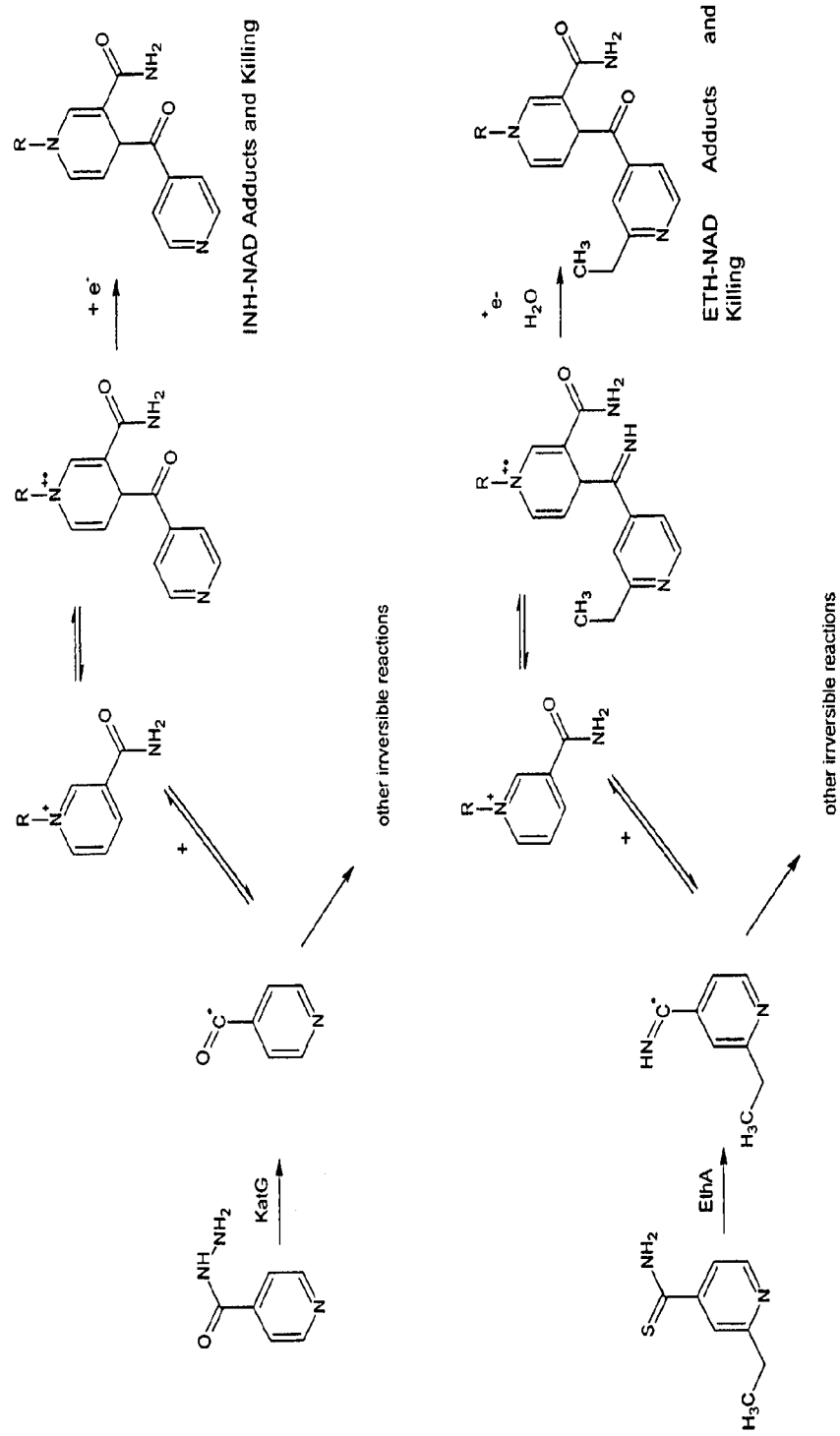
FIG. 1 shows a schematic comparison of a proposed mechanism of inactivation of *Mycobacterium* by isoniazid (top) compared to ethionamide (bottom). Note that the mechanisms are quite similar, resulting in similar adducts which produce similar results (inhibition of growth or death of *Mycobacterium*.
Figure 2:
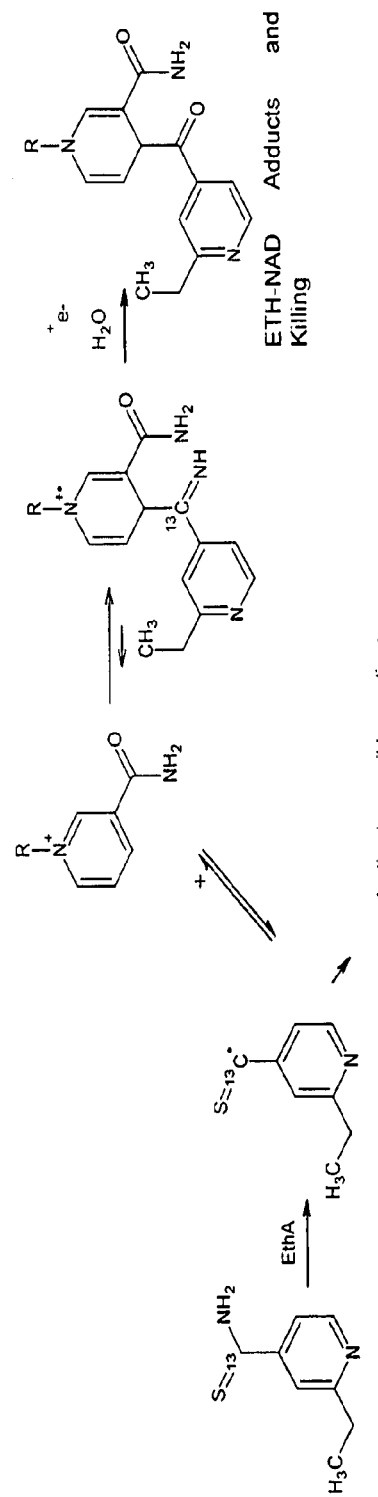
FIG. 2 shows how selective synthesis of isotopically labeled ethionamide, in this case, carbon-13 labeled ethionamide (or related compound), will result in more toxic adducts (a higher concentration of therapeutic toxic adducts) because of the shift in equilibrium toward the production of those toxic products.
Figure 3:
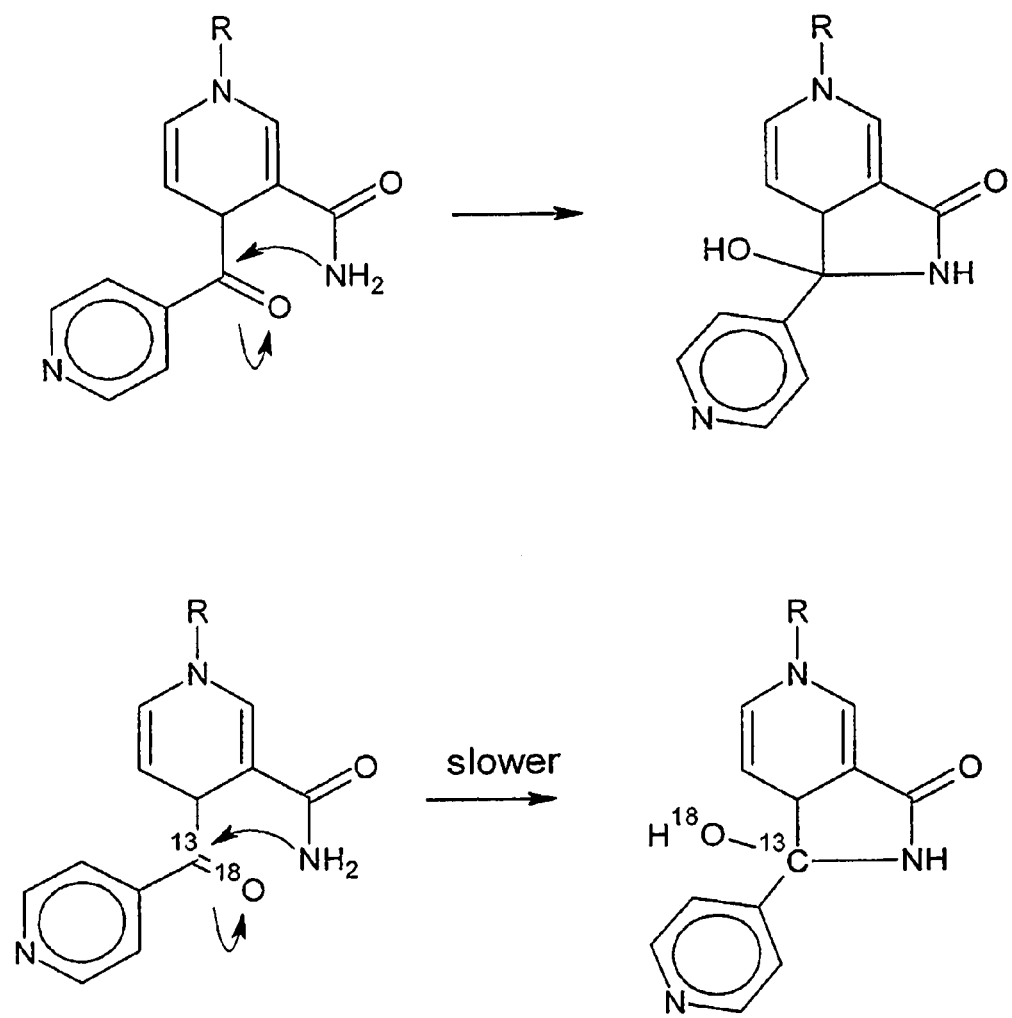
FIG. 3 shows how decrease rate of hemiamidal formation can be achieved through C and/or O heavy isotope replacement.

In certain aspects, the present invention relates to compounds according to the chemical structure:

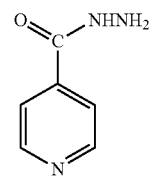

or a pharmaceutically acceptable salt thereof wherein the compound contains at least one isotopically labeled atom, preferably carbon-13, nitrogen-15 or oxygen-17 or oxygen-18 in the exocyclic acyl hydrazide moiety. It is noted that preferred compounds according to the present invention are labeled at positions where the labeled atom participates in a reaction to produce adduct formation in *Mycobacterium*. See FIG. 1, attached. Consequently, in preferred aspects of the invention, we provide for novel compounds based upon isoniazid (see below) which are isotopically labeled with carbon-13, oxygen-17, oxygen-18 nitrogen-15, which are preferably placed in the acyl hydrazide moiety of the compounds of interest.

In certain aspects, the present invention is directed to the following specific isotopically labeled compounds of isoniazid:

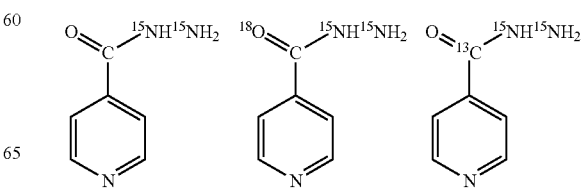

-continued

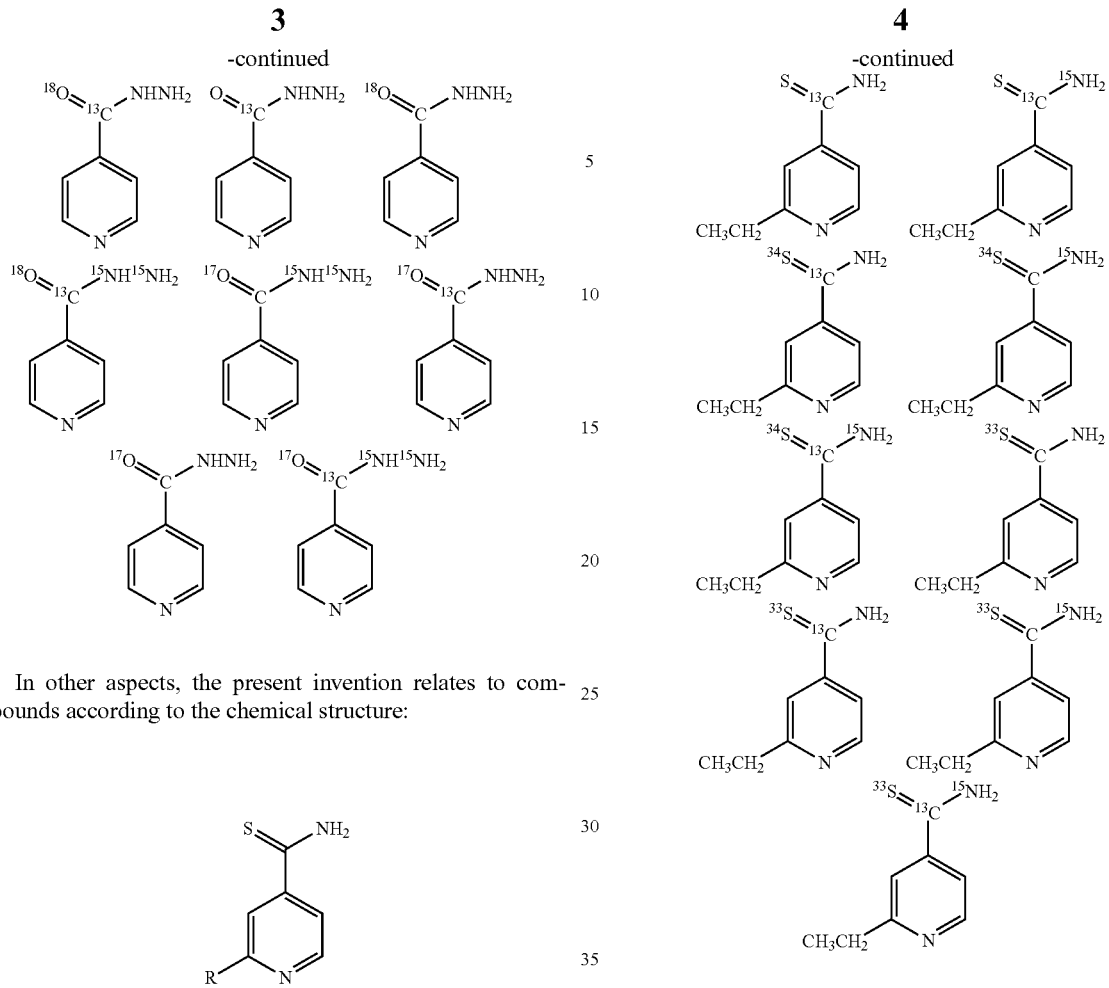

In other aspects, the present invention relates to compounds according to the chemical structure:

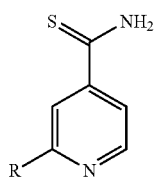

Where R is a $C_1$-$C_3$ alkyl group, preferably a $C_2$-$C_3$ alkyl group (ethionamide, propionamide), more preferably an ethyl group (ethionamide) or a pharmaceutically acceptable salt thereof wherein the compound contains at least one isotopically labeled atom, preferably carbon-13, nitrogen-15, sulfur-33 or sulfur-34 at the exocyclic thioamide position. It is noted that preferred compounds according to the present invention are labeled at positions where the labeled atom participates in a reaction to produce adduct formation in *Mycobacterium*. See FIG. 1, attached. Consequently, in preferred aspects of the invention, we provide for novel compounds based upon ethionamide which are isotopically labeled with carbon-13, sulfur-33, sulfur-34 or nitrogen-15, which are preferably placed in the thionamide moiety of the compounds of interest.

In certain aspects, the present invention is directed to the following specific isotopically labeled compounds of ethionamide:

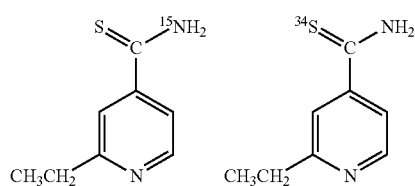

In addition, the present invention relates to pharmaceutical compositions comprising a therapeutically effective amount of an isotopically labeled compound as described above, in combination with a carrier, additive or excipient. Pharmaceutical dosage forms which can be administered in therapeutically effective dosages directly to the lungs where most *M. tuberculosis* infections occur are preferred as are oral dosage forms of compositions according to the present invention. Pharmaceutical compositions therefore relate to isotopically labeled compounds according to the present invention (e.g, isoniazid, ethionamide and/or propionamide) as otherwise disclosed herein at therapeutically effective dosages of at least 50 mg, 60 mg, 75 mg, 100 mg., 150 mg., 300 mg., alone, or optionally in combination with a therapeutically effective amount of at least one additional anti-tuberculosis agent. Such agents are exemplified by aminosalicyclic acid/aminosalicylate sodium, capreomycin sulfate, clofazimine, cycloserine, ethambutol hydrochloride (myambutol), kanamycin sulfate, pyrazinamide, rifabutin, rifampin, rifapentine, streptomycin sulfate, gatifloxacin and mixtures thereof, all in therapeutically effective amounts.

A particular pharmaceutical composition comprises therapeutically effective amounts of isotopically labeled isoniazid and/or ethionamide, preferably isoniazid (at least 50 mg, at least 60 mg, at least 75 mg, at least 100 mg, at least 150 mg. or 300 mg or more) in combination with a therapeutically effective amount of rifampin (at least 50 mg, at least 60 mg, at least 75 mg, at least 100 mg, at least 125 mg, at least 150 mg), pyrazinamide (at least 50 mg, at least 60 mg, at least 75 mg, at least 100 mg, at least 150 mg. or 300 mg) and optionally, ethambutol (at least 50 mg, at least 60 mg, at least 75 mg, at least 100 mg, at least 125 mg, at least 150 mg, at least 200 mg, at least 250 mg, at least 500 mg) or their pharmaceutically acceptable salts, in oral or parenteral dosage form. In addition to oral or parenteral routes, these compositions may also be adapted for delivery by a number of other routes as described hereinbelow, especially including a pulmonary route of administration.

Another particular pharmaceutical composition comprises isotopically labeled ethionamide (at least 50 mg, at least 60 mg, at least 75 mg, at least 100 mg, at least 150 mg. or 300 mg) in therapeutically effective amounts in combination with gatifloxacin (at least 50 mg, at least 60 mg, at least 75 mg, at least 100 mg, at least 150 mg. or 300 mg) and optionally pyrazinamide (at least 50 mg, at least 60 mg, at least 75 mg, at least 100 mg, at least 150 mg. or 300 mg) or their pharmaceutically acceptable salts, in oral or parenteral dosage form.

In method aspects of the present invention, compounds according to the present invention are used for the treatment of *Mycobacterium*, especially *Mycobacterium tuberculosis* infections in patients in need of therapy. The method comprises administering to a patient in need thereof, a therapeutically effective amount of an isotopically labeled compound according to the present invention (isoniazid, ethionamide or propionamide), alone or in combination with one agent selected from the group consisting of rifampin, pyrazinamide, ethambutol (as ethambutol hydrochloride), aminosalicyclic acid/aminosalicylate sodium, capreomycin sulfate, clofazimine, cycloserine, kanamycin sulfate, rifabutin, rifapentine, streptomycin sulfate, gatifloxacin and mixtures thereof, all in therapeutically effective amounts. Methods of treating *Mycobacterium*, especially *Mycobacterium tuberculosis* with isotopically labeled isoniazid, ethionamide or derivatives thereof are substantially more effective than treating these same infections with non-isotopically labeled compound.

In certain preferred aspects of the invention a patient or subject in need of therapy is administered therapeutically effective amounts of isotopically labeled isoniazid in combination with rifampin, pyrazinamide and optionally, ethambutol. In still other methods, a patient or subject in need of therapy is administered therapeutically effective amounts of isotopically labeled ethionamide in combination with therapeutically effective amounts of gatifloxacin and optionally pyrazinamide.

It has unexpectedly been discovered that the use of an isotopically labeled compound as otherwise disclosed herein is significantly more effective/active than non-isotopically labeled compound against *Mycobacterium* and in particular, *M. tuberculosis*. Thus, in certain aspects of the invention, compounds according to the present invention may be used to treat infection by *Mycobacterium*, in particular, *M. tuberculosis* at a level which is at least about 15%, at least about 20%, at least about 30%, at least about 35%, more active/effective than is treatment with an identical, but non-isotopically labeled compound. It has been discovered that the present compounds are more active because of increased inhibitory activity against *Mycobacterium* per se, as well as because of enhanced pharmacokinetics and/or bioavailability of the isotopically labeled compound in comparison to the non-isotopically labeled compound. Thus, in the present invention, the isotopically labeled compounds of the present invention exhibit a minimum inhibitory concentration and/or a minimum effective concentration in vitro and in vivo which is at least 15% lower, or at least about 20% lower than for the non-isotopically labeled compounds. The present compounds are thus significantly more active and effective against *Mycobacterium* infections and in particular, *M. tuberculosis* infections than the identical compounds which are non-isotopically labeled. This is unexpected.

DETAILED DESCRIPTION OF THE INVENTION

The following terms shall be used to describe the present invention. In instances where a term is not specifically defined herein, the term shall be accorded its meaning, within context, as understood by those of ordinary skill in the art.

The term "compound" shall mean any specific compound which is disclosed within this specification and typically means an isotopically labeled compound. Pharmaceutically acceptable salts (generally, pyridinium salts) are also compounds for use in the present invention. The term compound, as it relates to the present invention, also refers to isotopically labeled isoniazid, as well as compounds/derivatives of ethionamide, such as propionamide.

The term "effective" when used in context, shall mean any amount of a compound or component which is used to produce an intended result within the context of its use. In the case of compounds according to the present invention, the term effective generally refers to a therapeutically effective amount of compound which will inhibit the growth (bacteriastatic) and/or produce a die-off (bacteriacidal) of *Mycobacterium*. This term is distinguishable from a diagnostic effective amount of isoniazid and/or ethionamide which may be used short term (for example, a few hours) to diagnose the presence of a tuberculosis infection in a patient at risk. Agents useful in treating tuberculosis infections are treated with an amount and for a duration effective in treating (i.e., in eliminating or at least stabilizing) the tuberculosis infection in the patient.

In the present invention, isotopically labeled isoniazid, ethionamide and/or propionamide (preferably, isoniazid) according to the present invention is usually combined in therapeutically effective amounts with at least one and preferably more than one additional anti-tuberculosis agent selected from the group consisting of aminosalicyclic acid/aminosalicylate sodium, capreomycin sulfate, clofazimine, cycloserine, ethambutol hydrochloride, kanamycin sulfate, pyrazinamide, rifabutin, rifampin, rifapentine, streptomycin sulfate and mixtures thereof, all in therapeutically effective amounts. Therapeutically effective amounts of these agents generally range from as little as 1 mg/kg per day up to 50 mg/kg per day (100 mg up to several mg per day). Isoniazid and ethionamide are usually administered to a patient in therapeutically effective amounts ranging from about 5 mg/kg per day to about 20 mg/kg per day up to about 300-500 mg. In certain aspects Therapeutic compounds may be administered daily, several times a week (e.g. 5 times a week) or once or twice weekly. Therapy generally continues for at least several weeks to 2 months and up to a year or more depending upon the severity of the infection and the response of the patient to therapeutic intervention.

A typical oral dose of isoniazid and/or ethionamide is at least about 25 mg and is preferably at least about 50 mg. An oral dosage form of at least 75 mg of isoniazid or ethionamide or 100 mg may be given up to 3 to 4 times daily (QID).

In certain preferred aspects, therapy may have a minimum duration of 6 months (26 weeks), and consist of an initial intensive phase (2 months) and a continuation phase (usually either 4 or 7 months).

Isotopically labeled isoniazid and/or ethionamide may be combined with effective amounts of pyridoxine (Hexa-beta-lin), 10-50 mg/kg per day or more, in order to reduce the side effects of isoniazid/ethionamide therapy.

In a preferred method of treating previously untreated patients infected with tuberculosis, a combination of isoniazid-rifampin-pyrazinamide-ethambutol is utilized in therapeutically effective amounts to treat the patient. In this aspect of the invention, isoniazid is generally used at a concentration of about 5-10 mg/kg per day up to about 300 mg (or more, depending of the weight of the patient) per day. Rifampin is used at a concentration ranging from about 10 to 20 mg/kg per day up to about 600 mg per day. Pyrazinamide is used at a concentration ranging from about 15 to 30 mg/kg per day up to about 2 grams. Ethambutol is used at a concentration ranging from about 10 to 25 mg/kg per day up to about 1 gram.

In other embodiments, a combination of ethionamide and gatifloxacin in therapeutically effective amounts with or without pyrazinamide may be used to treat tuberculosis. In this aspect of the invention, ethionamide in therapeutically effective amounts (about 5-25 mg/kg per day) and gatifloxacin (15-100 mg/kg per day) are used in amounts generally ranging from about several hundred mg per day or more up to several grams per day.

The following table represents a series of recommended therapeutic approaches to tuberculosis therapy. All of the therapies indicated in table 1 include the use of isoniazid. The present isotopically labeled isoniazid compound may be substituted for indicated isoniazid. These are recommended therapies. The approach to tuberculosis therapy may be varied to provide effective approaches. Ethionamide may be substituted for isoniazid at slightly higher dosages.

TABLE 1

Recommended Regimens[1a] for Culture-Positive, Drug-Susceptible Pulmonary Tuberculosis

| Initial Phase | Continuation Phase | Drugs[1b] | Dosing Interval and Doses[1c] (minimum duration) | Total Doses for Both Phases (total minimum duration) |
|---|---|---|---|---|
| Regimen 1 | | INH-RIF-PZA-EMB | 7 days/wk for 56 doses (8 wks) OR 5 days/wk for 40 doses (8 wks) | |
| | 1a | INH-RIF | 7 days/wk for 126 doses (18 wks) OR 5 days/wk for 90 doses (18 wks)[1d] | 7 days/wk = 182 doses OR 5 days/wk = 130 doses (total 26 wks) |
| | 1b | INH-RIF | twice weekly for 36 doses (18 wks)[1d 1e] | 7 days/wk initially = 92 doses OR 5 days/wk initially = 76 doses (total 26 wks) |
| | 1c[1f] | INH-RPT | once weekly for 18 doses (18 wks)[1d] | 7 days/wk initially = 74 doses OR 5 days/wk initially = 58 doses (total 26 wks) |
| Regimen 2 | | INH-RIF-PZA-EMB | 7 days/wk for 14 doses (2 wks) then twice weekly for 12 doses (6 wks) OR 5 days/wk for 10 doses (2 wks) then twice weekly for 12 doses (6 wks) | |
| | 2a | INH-RIF | twice weekly for 36 doses (18 wks)[1d 1e] | 7 days/wk initially = 62 doses OR 5 days/wk initially = 58 doses (total 26 wks) |
| | 2b[1f] | INH-RPT | once weekly for 18 doses (18 wks)[1d] | 7 days/wk initially = 44 doses OR 5 days/wk initially = 40 doses (total 26 wks) |
| Regimen 3 | | INH-RIF-PZA-EMB | 3 times weekly for 24 doses (8 wks) | |
| | 3a | INH-RIF | 3 times weekly for 54 doses (18 wks)[1d] | 78 doses (total 26 wks) |
| Regimen 4 | | INH-RIF-EMB | 7 days/wk for 56 doses (8 wks) OR 5 days/wk for 40 doses (8 wks) | |
| | 4a | INH-RIF | 7 days/wk for 217 doses (31 wks) OR 5 days/wk for 155 doses (31 wks)[1d] | 7 days/wk initially = 273 doses OR 5 days/wk initially = 195 doses (total 39 wks) |
| | 4b | INH-RIF | twice weekly for 62 doses (31 wks)[1d] | 7 days/wk initially = 118 doses OR 5 days/wk initially = 102 doses (total 39 wks) |

[1a]Each regimen consists of an initial phase and a continuation phase; Regimen 1 has 3 possible continuation phases (a, b, c), Regimens 2 and 4 have 2 possible continuation phases (a, b), and Regimen 3 has 1 recommended continuation phase (a).
[1b]INH = isoniazid; RIF = rifampin; PZA = pyrazinamide; EMB = ethambutol; RPT = rifapentine
[1c]Daily regimen = 7 days/wk; drugs can be given 5 days/wk if directly observed therapy (DOT) is used (this can be considered a daily regimen and total required number of doses is lowered accordingly). Continuation phase regimens given 2 or 3 times weekly should be given using DOT.
[1d]Patients with cavitation on initial chest radiograph who still have positive cultures at completion of the initial phase (2 months) should receive a 7-month (31-week) continuation phase consisting of 217 doses (7 days/wk) or 62 doses (twice weekly)
[1e]Continuation phase regimens 1b and 2a are not recommended for HIV-infected patients who have CD4+ counts less than 100/mm$^3$
[1f]Continuation phase regimens 1c and 2b should be used only in HIV-negative patients who have negative sputum smears at completion of the initial phase at 2 months (8 wks) and who do not have cavitation on initial chest radiograph. If patients are started on one of these regimens and the 2-month culture is found to be positive, the continuation phase should be extended an extra 3 months.

The term "isotopically labeled" shall mean isotopically labeled with carbon-13, nitrogen-15, sulfur-33, sulfur-34, oxygen-17, oxygen-18 at positions on the compound (exocyclic positions), preferably positions which are involved in reactions which produce toxic adducts to *Mycobacterium*.

The term "*Mycobacterium*", is used to describe a genus of Actinobacteria, given its own family, the Mycobacteriaceae. The genus includes pathogens known to cause serious diseases in mammals, including tuberculosis and leprosy. The Latin prefix "myco-" means both fungus and wax; its use here relates to the "waxy" compounds in the cell wall. *Mycobacteria* are aerobic and nonmotile bacteria (except for the species *Mycobacterium marinum* which has been shown to be motile within macrophages) that are characteristically acid-alcohol fast.[1] *Mycobacteria* do not contain endospores or capsules, and are usually considered Gram-positive. While mycobacteria do not seem to fit the Gram-positive category from an empirical standpoint (i.e. they do not retain the crystal violet stain), they are classified as an acid-fast Gram-positive bacterium due to their lack of an outer cell membrane. All *Mycobacterium* species share a characteristic cell wall, thicker than in many other bacteria, which is hydrophobic, waxy, and rich in mycolic acids/mycolates. The cell wall makes a substantial contribution to the hardiness of this genus.

Many *Mycobacterium* species adapt readily to growth on very simple substrates, using ammonia or amino acids as nitrogen sources and glycerol as a carbon source in the presence of mineral salts. Optimum growth temperatures vary widely according to the species and range from 25° C. to over 50° C.

Some species can be very difficult to culture (i.e. they are fastidious), sometimes taking over two years to develop in culture. Further, some species also have extremely long reproductive cycles—*M. leprae* (leprosy), may take more than 20 days to proceed through one division cycle (for comparison, some *E. coli* strains take only 20 minutes), making laboratory culture a slow process.

A natural division occurs between slowly- and rapidly-growing species. *Mycobacteria* that form colonies clearly visible to the naked eye within 7 days on subculture are termed rapid growers, while those requiring longer periods are termed slow growers. *Mycobacteria* are slightly curved or straight rods between 0.2-0.6 μm wide by 1.0-10 μm long.

A particularly important *Mycobacterium* species to the present invention is *M. tuberculosis*. The term "Tuberculosis" or "TB" is used to describe the infection caused by the infective agent "*Mycobacterium tuberculosis*" or "*M. tuberculosis*", a tubercle *bacillus* bacteria. Tuberculosis is a potentially fatal contagious disease that can affect almost any part of the body but is most frequently an infection of the lungs. It is caused by a bacterial microorganism, the tubercle *bacillus* or *Mycobacterium tuberculosis.*

Tuberculosis is primarily an infection of the lungs, but any organ system is susceptible, so its manifestations may be varied. Effective therapy and methods of control and prevention of tuberculosis have been developed, but the disease remains a major cause of mortality and morbidity throughout the world. The treatment of tuberculosis has been complicated by the emergence of drug-resistant organisms, including multiple-drug-resistant tuberculosis, especially in those with HIV infection.

*Mycobacterium tuberculosis*, the causative agent of tuberculosis, is transmitted by airborne droplet nuclei produced when an individual with active disease coughs, speaks, or sneezes. When inhaled, the droplet nuclei reach the alveoli of the lung. In susceptible individuals the organisms may then multiply and spread through lymphatics to the lymph nodes, and through the bloodstream to other sites such as the lung apices, bone marrow, kidneys, and meninges.

The development of acquired immunity in 2 to 10 weeks results in a halt to bacterial multiplication. Lesions heal and the individual remains asymptomatic. Such an individual is said to have tuberculous infection without disease, and will show a positive tuberculin test. The risk of developing active disease with clinical symptoms and positive cultures for the tubercle *bacillus* diminishes with time and may never occur, but is a lifelong risk. Approximately 5% of individuals with tuberculous infection progress to active disease. Progression occurs mainly in the first 2 years after infection; household contacts and the newly infected are thus at risk.

Many of the symptoms of tuberculosis, whether pulmonary disease or extrapulmonary disease, are nonspecific. Fatigue or tiredness, weight loss, fever, and loss of appetite may be present for months. A fever of unknown origin may be the sole indication of tuberculosis, or an individual may have an acute influenzalike illness. Erythema nodosum, a skin lesion, is occasionally associated with the disease.

The lung is the most common location for a focus of infection to flare into active disease with the acceleration of the growth of organisms. Infections in the lung are the primary focus of the present invention. There may be complaints of cough, which can produce sputum containing mucus, pus-and, rarely, blood. Listening to the lungs may disclose rales or crackles and signs of pleural effusion (the escape of fluid into the lungs) or consolidation if present. In many, especially those with small infiltration, the physical examination of the chest reveals no abnormalities.

Miliary tuberculosis is a variant that results from the blood-borne dissemination of a great number of organisms resulting in the simultaneous seeding of many organ systems. The meninges, liver, bone marrow, spleen, and genitourinary system are usually involved. The term miliary refers to the lung lesions being the size of millet seeds (about 0.08 in. or 2 mm). These lung lesions are present bilaterally. Symptoms are variable.

Extrapulmonary tuberculosis is much less common than pulmonary disease. However, in individuals with AIDS, extrapulmonary tuberculosis predominates, particularly with lymph node involvement, with some pulmonary impact. For example, fluid in the lungs and lung lesions are other common manifestations of tuberculosis in AIDS. The lung is the portal of entry, and an extrapulmonary focus, seeded at the time of infection, breaks down with disease occurring.

Development of renal tuberculosis can result in symptoms of burning on urination, and blood and white cells in the urine; or the individual may be asymptomatic. The symptoms of tuberculous meningitis are nonspecific, with acute or chronic fever, headache, irritability, and malaise.

A tuberculous pleural effusion can occur without obvious lung involvement. Fever and chest pain upon breathing are common symptoms. Bone and joint involvement results in pain and fever at the joint site. The most common complaint is a chronic arthritis usually localized to one joint. Osteomyelitis is also usually present. Pericardial inflammation with fluid accumulation or constriction of the heart chambers secondary to pericardial scarring are two other forms of extrapulmonary disease.

At present, the principal methods of diagnosis for pulmonary tuberculosis are the tuberculin skin test (an intracutaneous injection of purified protein derivative tuberculin is performed, and the injection site examined for reactivity), sputum smear and culture, and the chest x-ray. Culture and biopsy are important in making the diagnosis in extrapulmonary disease.

A combination of two or more drugs is often used in the initial traditional therapy of tuberculous disease. Drug combinations are used to lessen the chance of drug-resistant organisms surviving. The preferred treatment regimen for both pulmonary and extrapulmonary tuberculosis is a 6-month regimen of the antibiotics isoniazid, rifampin, and pyrazinamide given for 2 months, followed by isoniazid and rifampin for 4 months. Because of the problem of drug-resistant cases, ethambutol can be included in the initial regimen until the results of drug susceptibility studies are known. Once treatment is started, improvement occurs in almost all individuals. Any treatment failure or individual relapse is usually due to drug-resistant organisms.

The present invention relates to novel compounds according to the chemical structure:

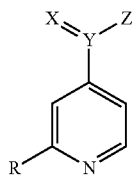

Where
X is an oxygen or a sulfur atom selected from the group consisting of $^{16}O$, $^{17}O$, $^{18}O$, $^{32}S$, $^{33}S$ and $^{34}S$;
Y is a carbon atom selected from the group consisting of $^{12}C$ and $^{13}C$;
Z is a $NH_2$ group or a $NHNH_2$ group, which group is optionally isotopically labeled with at least one $^{15}N$ atom, preferably two $^{15}N$ atoms in the case of a $NHNH_2$ group;
R is H or a $C_1$-$C_3$ alkyl group, preferably H or an ethyl group, with the proviso that R is H and Z is an optionally isotopically labeled $NHNH_2$ group when X is an oxygen atom and R is a $C_1$-$C_3$ alkyl group, preferably an ethyl group and Z is an optionally isotopically labeled $NH_2$ group when X is a sulfur atom;
Wherein at least one of X, Y and Z is isotopically labeled, or a pharmaceutically acceptable salt thereof.

In certain aspects, the present invention relates to compounds according to the chemical structure:

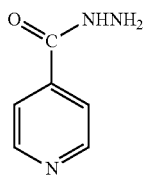

or a pharmaceutically acceptable salt thereof wherein the compound contains at least one isotopically labeled atom, preferably carbon-13, nitrogen-15 or oxygen-17 or oxygen-18 at the exocyclic acyl hydrazide position. It is noted that preferred compounds according to the present invention are labeled at positions where the labeled atom participates in a reaction to produce adduct formation in Mycobacterium. See FIG. 1, attached. Consequently, in preferred aspects of the invention, we provide for novel compounds based upon isoniazid (see below) which are isotopically labeled with carbon-13, sulfur-34 or nitrogen-15, which are preferably placed in the acyl hydrazide moiety of the compounds of interest.

In certain aspects, the present invention is directed to the following specific isotopically labeled compounds of isoniazid:

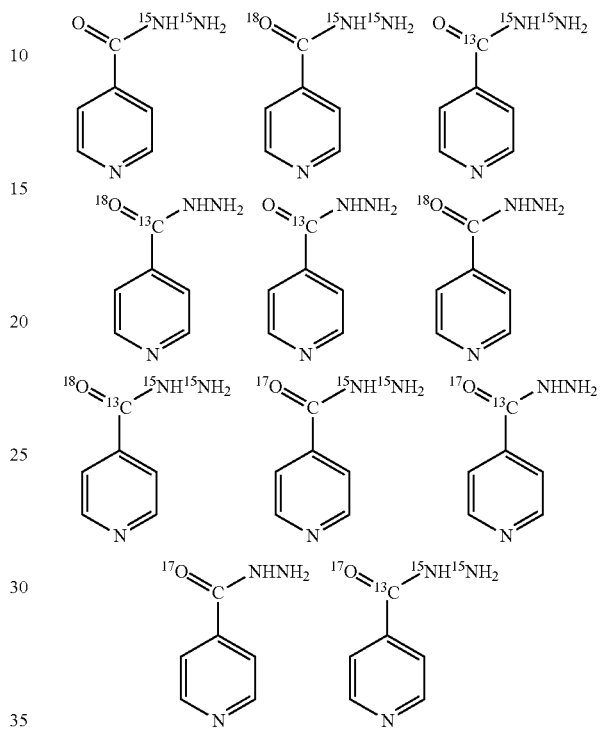

In other aspects, the present invention relates to compounds according to the chemical structure:

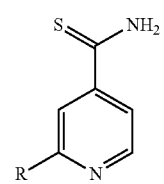

Where R is a $C_1$-$C_3$ alkyl group, preferably a $C_2$-$C_3$ alkyl group (ethionamide, propionamide), more preferably an ethyl group (ethionamide) or a pharmaceutically acceptable salt thereof wherein the compound contains at least one isotopically labeled atom, preferably carbon-13, nitrogen-15, sulfur-33 or sulfur-34 at the exocyclic thioamide position. It is noted that preferred compounds according to the present invention are labeled at positions where the labeled atom participates in a reaction to produce adduct formation in Mycobacterium. See FIG. 1, attached. Consequently, in preferred aspects of the invention, we provide for novel compounds based upon ethionamide which are isotopically labeled with carbon-13, sulfur-33, sulfur-34 or nitrogen-15, which are preferably placed in the thionamide moiety of the compounds of interest.

In certain aspects, the present invention is directed to the following specific isotopically labeled compounds of ethionamide:

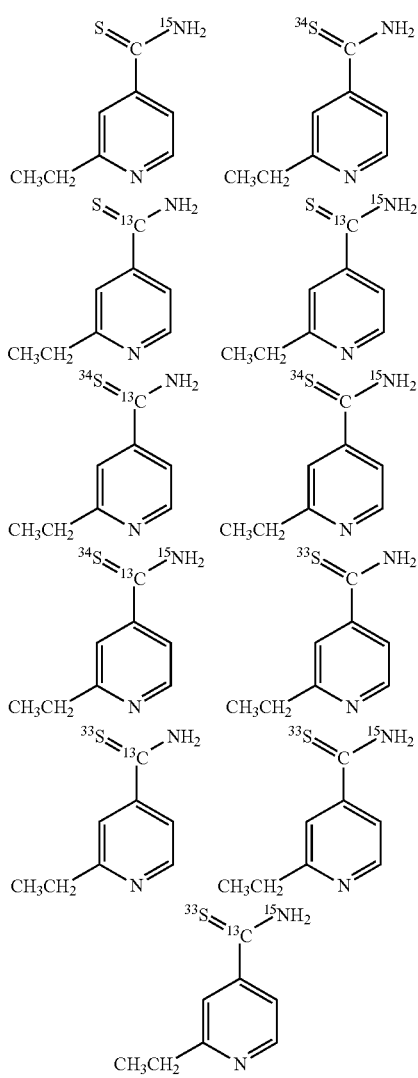

Compounds according to the present invention may be used in pharmaceutical compositions having biological/pharmacological activity for the treatment of, for example, *Mycobacterial* infections, including a number of other conditions and/or disease states which may appear or occur secondary to the bacterial infection. These compositions comprise an effective amount of any one or more of the compounds disclosed hereinabove, optionally in combination with a pharmaceutically acceptable additive, carrier or excipient. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously. Preferred routes of administration include oral administration and pulmonary administration (by inhaler/inhalation spreay).

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application. Suitable topical formulations are readily prepared for each of these areas or organs.

Topical application also can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound of the instant invention that may be combined with the carrier materials to produce a single dosage form will vary depending upon the host treated, the particular mode of administration. Preferably, the compositions should be formulated so that a therapeutically effective dosage of between about 1 and 25 mg/kg, about 5 to about 15 mg/kg of patient/day of the novel compound can be administered to a patient receiving these compositions. Preferably, pharmaceutical compositions in dosage form according to the present invention comprise a therapeutically effective amount of at least 25 mg of isotopically labeled compound, at least 50 mg of isotopically labeled compound, at least 60 mg of isotopically labeled compound, at least 75 mg of isotopically labeled compound, at least 100 mg of isotopically labeled, at least 150 mg of isotopically labeled compound, at least 200 mg of isotopically labeled compound, at least 250 mg of isotopically labeled compound, at least 300 mg of isotopically labeled compound, about 350 mg of isotopically labeled compound, about 400 mg of isotopically labeled compound, about 500 mg of isotopically labeled compound, about 750 mg of isotopically labeled compound, about 1 g (1000 mg) of isotopically labeled compound, alone or in combination with a therapeutically effective amount of at least one additional anti-tuberculosis agent. Exemplary additional anti-tuberculosis agents which may be used in pharmaceutical compositions include one or more of aminosalicyclic acid/aminosalicylate sodium, capreomycin sulfate, clofazimine, cycloserine, ethambutol hydrochloride (myambutol), kanamycin sulfate, pyrazinamide, rifabutin, rifampin, rifapentine, streptomycin sulfate, gatifloxacin and mixtures thereof, all in therapeutically effective amounts.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral or inhalation (intratracheal) administrations per day (for example, B.I.D. or Q.I.D.) and may include oral, pulmonary, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl alkyl nucleosides or phosphate ester pro-drug forms of the nucleoside compounds according to the present invention.

The present invention also relates to pharmaceutical compositions in oral dosage form comprising therapeutically effective amounts of isotopically labeled compound according to the present invention, optionally in combination with a pharmaceutically acceptable carrier, additive or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

In preferred aspects of the invention, especially for treatment of *M. tuberculosis* infections, the compound is administered to the lungs of the subject via pulmonary administration, including intratracheal administration. The pharmaceutical composition of the invention for pulmonary administration is usually used as an inhalant. The composition can be formed into dry powder inhalants, inhalant suspensions, inhalant solutions, encapsulated inhalants and like known forms of inhalants. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable.

When the pharmaceutical composition of the invention is used in the form of a powder, the mean particle diameter of the powder is not especially limited but, in view of the residence of the particles in the lungs, is preferably that the particles fall within the range of about 0.1 to 20 µm, and particularly about 1 to 5 µm. Although the particle size distribution of the powder pharmaceutical composition of the invention is not particularly limited, it is preferable that particles having a size of about 25 µm or more account for not more than about 5% of the particles, and preferably, 1% or less to maximize delivery into the lungs of the subject.

The pharmaceutical composition in the form of a powder of the invention can be produced by, for example, using the drying-micronization method, the spray drying method and standard pharmaceutical methodology well known in the art.

By way of example without limitation, according to the drying-pulverization method, the pharmaceutical composition in the form of a powder can be prepared by drying an aqueous solution (or aqueous dispersion) containing the compound or mixtures with other active agents thereof and excipients which provide for immediate release in pulmonary tissue and microparticulating the dried product. Stated more specifically, after dissolving (or dispersing) a pharmaceutically acceptable carrier, additive or excipient in an aqueous medium, compounds according to the present invention in effective amounts are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing isoniazid, urea or mixtures thereof and excipients, additives or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isoniazid, urea or mixtures thereof that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled compound alone or in mixtures with other compounds according to the present invention or with other anti-Mycobacterial agents. As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of compound according to the present invention which is included in the final composition.

The pharmaceutical compositions of the invention are safe and effective for use in the therapeutic methods according to the present invention. Although the dosage of the composition of the invention may vary depending on the type of active substance administered (isoniazid, ethionamide, propionamide and optional additional anti-tuberculosis agents) as well as the nature (size, weight, etc.) of the subject to be diagnosed, the composition is administered in an amount effective for allowing the pharmacologically active substance to be cleaved to cleavage products to be measured. For example, the composition is preferably administered such that the active ingredient (isotopically labeled compound) can be given to a human adult in a dose of at least about 25 mg, at least about 50 mg, at least about 60 mg, at least about 75 mg., at least about 100 mg, at least about 150 mg, at least about 200 mg, at least about 250 mg, at least about 300 mg, at least about 350 mg, at least about 400 mg, at least about 500 mg, at least about 750 mg, at least about 1000 mg, and given in a single dose, including sustained or controlled release dosages once daily.

The form of the pharmaceutical composition of the invention such as a powder, solution, suspension etc. may be suitably selected according to the type of substance to be administered.

As an administration route, direct inhalation via the mouth using an inhaler is usually administered into the airways and in particular, directly to pulmonary tissue, the active substance contained therein produces immediate effects. Furthermore, the composition is formulated as an immediate release product so that cleavage and analysis can begin soon after administration.

Compounds according to the present invention may be readily synthesized using methods which are readily available in the art. For example, the present compounds may be synthesized by analogy to synthetic approaches which are used to synthesize isotopically labeled isoniazid by modifying the synthetic route which is described in: Schantl J and Gstach H, *Synthesis* (Stuttgart) 1980 (9) pp 694-695. Other methods are readily available in the art for producing all of the compounds which are described herein.

Starting from pyridine (isoniazid) or 2-alkylpyridine (ethionamide) an ice cooled solution of $Br_2$ neat or in solvent is made. To this a solution of benzophenone-arylhydrazone in absolute (methylene chloride) is added dropwise over a period of approximately 30 minutes at 0-5° C. Seeding crystals of the intermediate salt is made, to which is added isotopically labeled (e.g. carbon-13) potassium cyanide. The cyanide is introduced in the 4-position (para) of the pyridine or alkylpyridine. The isotopically labeled 4-cyano-2-alkylpyridine compound may be further modified to isotopically labeled isoniazid, ethionamide or its derivatives. The resulting compound may have isotopically labeled atoms at virtually every point in the molecule, but preferably has isotopically labeled atoms in the acylhydrazide or thionamide group, because these are the groups are shown to significantly influence the activity of isotopically labeled compounds according to the invention.

There are multiple ways to make ethionamide from the cyanopyridine, such that various positions in the molecule is isotopically labeled. Characterization is by TLC against known standards and by NMR.

Chemical Synthesis

Preparation of $^{13}C$ Acyl isoniazid is via a modification of the method of Feely and Beavers *J. Am. Chem. Soc.* 1959, 81, 4004-4007. 4-[$^{13}C$]cyanopyridine: The synthesis of 1-(n-nonyloxy)-pyridinium iodide was accomplished according to the method of Feely and Beavers. The subsequent method for the generation of the cyanopyridine was modified as follows. $Bu_4N^{13}CN$ (3.00 g, 11.1 mmol) was dissolved in 20 mL of $H_2O$ at room temperature. A solution of 1-(n-nonyloxy)-pyridinium iodide (3.90 g, 11.1 mmol) in 13 mL of $H_2O$ was added and a bright yellow frothy layer separates over a period of a few minutes. The water layer was monitored by $^{13}C$ NMR and after 24 h the relative amount of $Bu_4N^{13}CN$ in solution is minimized and stable. $Et_3N$ (0.9 mL) was added and the mixture was stirred 5 min, then extracted with $CH_2Cl_2$. The combined organic extracts were extracted with 1M HCl, following which the combined acidic extracts were neutralized with conc'n $Na_2CO_3$ in $H_2O$ and again extracted with $CH_2Cl_2$. The organic layer was dried ($Na_2SO_4$), filtered, and the solvent was evaporated. The crude material was purified by column chromatography (10% EtOAc in hexanes) to give 480 mg (41% yield) of product as a white crystalline solid, Mp 77.5-79.5° C. (Lit.[1] 78-80° C.). $^1H$ NMR matched literature values; $^{13}C$ NMR ($CDCl_3$) δ 150.8 (d, J=4.9 Hz), 125.2 (d, J=2.0 Hz), 120.5 (d, J=81.7 Hz), 116.4; Anal. Calcd for $C_5^{13}CH_4N_2$: C, 69.51; H, 3.84; N, 26.65. Found: C, 69.45; H, 3.73; N, 29.26. HRMS m/z 106.04800 (M+1 for M=105.04). Alternatively, the ethylpyridinium chloride, and potassium cyanide have been used.

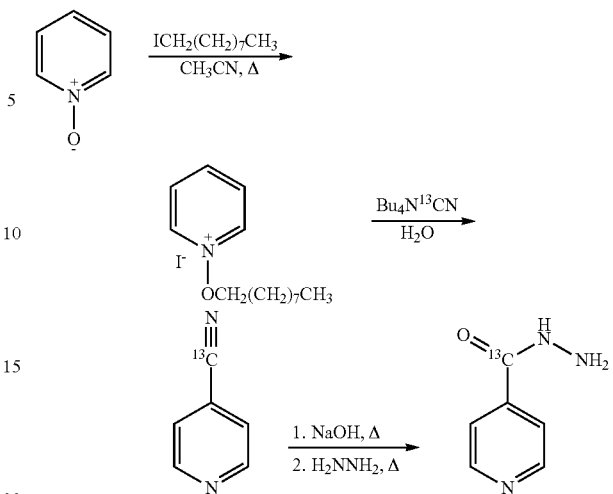

An alternative to the above method for cyanopyridine synthesis is derived from the synthetic route in: Schantl J and Gstach H, *Synthesis* (Stuttgart), 1980 (9) pp 694-695.

An ice cooled solution of $Br_2$ (9.99 g, 62.5 mmol) in absolute pyridine (35 ml) is made. To this a solution of benzophenone-arylhydrazone (62.5 mmol) in absolute $CH_2Cl_2$ (70 ml) is added drop wise over 30 minutes at 0-5° C. Continue stirring over ice for a further 30 minutes. To this, add 300 ml absolute Ether, and stir with ice, cooling for 90 minutes.

To make seeding crystals, take 2 ml of reaction mixture, add ether and scratch. Add seed crystals to major portion, harvest by filtration. Wash crystals with ether (~250 ml) remove solvent under vacuum. Yield 97%.

The above salt (5.42 mmol) is overlayed with ether (30 ml), KCN (1.41. g) in 5 ml water is added, and the phases mixed vigorously with a flask shaker. The solid phase will disappear of 10-30 minutes. To this then add a further 10 ml of water, and rotary evaporate off the ether. The remaining mix of a yellow oil and water is shaken for 5 hours, will decolorize as cyanopyridine and the benzophenonearylhydrazone reform. (This happens faster if catalytic alkali sodium ethoxide/ethanol is added). The resultant crystals of the benzophenonehydrazone are removed by filtration.

The water solution is saturated with NaCl, 40 mg activated charcoal added, and mixed 10 mins, and filtered through celite. The filtrate is extracted 4×25 ml with Ether, the organic layers pooled, dried with magnesium sulfate, and dried to produce 4-cyanopyridine. This is washed with petroleum ether (40-60° C. fraction) and dried. Yield—75%.

There are multiple ways to make isoniazid from the cyanopyridine. One can use Nguyen et al (*Chembiochem* 2001 2 877-883) a modification of Gasson's synthesis (USPTO 2830994). Characterization was by TLC against known standards and by NMR. Acyl $^{17}O$ or $^{18}O$ can be incorporated by use of $H_2^{17}O$ or $H_2^{18}O$ at this time, either with $^{13}C$ enrichment or independently, if desired. $^{15}N$ may be introduced through the 4-cyano group or an isotopically labeled hydrazine precursor which can be added to form the acyl hydrazide.

As an example, Isoniazid is well synthesized by this procedure:

4-pyridine-[$^{13}C$]carboxylic acid hydrazide: 4-[$^{13}C$]Cyanopyridine (400 mg, 3.80 mmol) was combined with 0.6 mL of $H_2O$. The slurry was heated to 40° C. and aq. NaOH (8%, 0.125 mL) was added dropwise over 30 min. After the slurry formed a slightly yellow solution it was heated to reflux for 1 h. The solution was cooled to ~90° C. and $H_2NNH_2$ (65-68% in H$_2$O, 0.75 mL, ~15 mmol) was carefully added dropwise over 20 min. Heated the solution to 104° C. for 3 h. The mixture was then cooled the solvent evaporated. The residue was taken up in a minimum amount of boiling methanol and activated charcoal was added. The hot mixture was filtered and cooled to 0° C. overnight. Precipitated crystals were recovered by filtration and washed with ice cold methanol. After drying under vacuum, 180 mg (34% yield) of product was obtained as clear needles, Mp 169.0-171.0° C. (Lit. 171-173° C.). Concentration of the mother liquor and recrystallization provided an additional 39 mg (7.4%, 41% total yield) of product with identical melting point. $^1$H NMR matched literature values; $^{13}$C NMR (D$_2$O) δ 170.3, 149.2 (d, J=3.6 Hz), 141.0 (d, J=61.9 Hz), 121.6 (d, J=2.2 Hz); Anal. Calcd for C$_5$$^{13}$CH$_7$N$_3$O: C, 52.89; H, 5.11; N, 30.42. Found: C, 52.67; H, 5.09; N, 33.98. HRMS m/z 139.06944 (M+1 for M=138.06).

Isotopically labeled ethionamide may be made by analogy the 4-cyanopyridine derivative (with 2-alkyl substitution) using H$_2$$^{33}$S or H$_2$$^{34}$S to introduce the isotopically labeled sulfur at the thioamide position and $^{15}$N may be introduced through the 4-cyano group or through isotopically labeled $^{15}$NH$_3$. Thus, the starting material would alternately be (compared to isoniazid) 2-alkyl-pyridine-N-oxide (where alkyl=C$_1$ to C$_3$), producing the analaogous cyanaopyridine. Treatment with H$_2$S affords the labeled Ethionamide.

BIOLOGICAL ACTIVITY

Example 1

Triplicate cultures of the vaccine strain of TB (M bovis BCG) were treated with 0 1 micrograms per ml of either "normal" $^{12}$C isoniazid, or of isoniazid enriched >95% with $^{13}$C at the acyl carbon and grown as conventionally. At 3 or 4 days after treatment, the antimicrobial effects of the $^{12}$C and $^{13}$C, compounds were evaluated by determining the cultures optical density. A significant increase in activity was seen for the $^{13C}$ labeled compound.

To confirm the optical density data, the cultures at day 4 were plated out for CFU (colony forming units): again, the marked expected increase in activity of the $^{13}$C-acyl compound was clear.

Example 2

The following method may be used to test the anti-tuberculosis activity of compounds of the present invention
1. Prepare 2.5 ml of 7H9 broth in 15.0 ml conical tubes containing each drug concentration. 'heavy' INH is taken at the following concentrations (in μg/ml): 0.1, 0.05, 0.025, 0.0125, and 0 (in duplicate). Isoniazid is taken as a control drug at 0.05 μg/ml concentration. 50 ul of 10 ug/ml is added in each tube and then serially diluted.
2. Add 10$^5$ bacilli of H37Rv to each tube and place the tubes at 37° C. incubator without shaking.
3. On day 0, determine actual CFU counts of the inoculum. Plate 0.1 ml of inoculum at 10$^3$ and 10$^4$ on 7H11 plain plates.
4. Do a visual analysis of the growth of bacilli in different drug concentrations on days 0, 7 and 14.
5. On day 14, plate the cultures from the tubes with no growth on plain 7H11 plates. Dilutions to be used 1:1 and 1:100.

Results:
For the MIC experiment following are the results
Day 7

| Drug concentration (ug/ml) | C13 INH | O18 INH | N15 INH | C12 INH | ETH |
|---|---|---|---|---|---|
| 0.0 | ++ | ++ | ++ | ++ | ++ |
| 0.0125 | + | + | + | + | ++ |
| 0.025 | ---- | ---- | ---- | −/+ | ++ |
| 0.05 | ---- | ---- | ---- | ---- | ++ |
| 0.1 | ---- | ---- | ---- | ---- | ++ |

Day 14

| Drug concentration (ug/ml) | C13 INH | O18 INH | N15 INH | C12 INH | ETH |
|---|---|---|---|---|---|
| 0.0 | +++ | +++ | +++ | +++ | +++ |
| 0.0125 | + | + | + | ++ | +++ |
| 0.025 | ---- | ---- | ---- | + | +++ |
| 0.05 | ---- | ---- | ---- | ---- | +++ |
| 0.1 | ---- | ---- | ---- | ---- | +++ |

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a compound" includes a plurality of compounds, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

The invention claimed is:

1. A compound having the chemical structure:

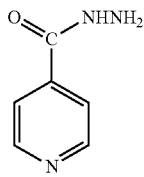

or a pharmaceutically acceptable salt thereof wherein the compound contains at least one isotopically labeled atom selected from the group consisting of carbon-13, oxygen-17 and oxygen-18 in the exocyclic acyl hydrazide moiety of the compound and said $NH_2NH_2$ group is optionally isotopically labeled with at least one $^{15}N$ atom.

2. A compound according to claim 1 having the chemical structure:

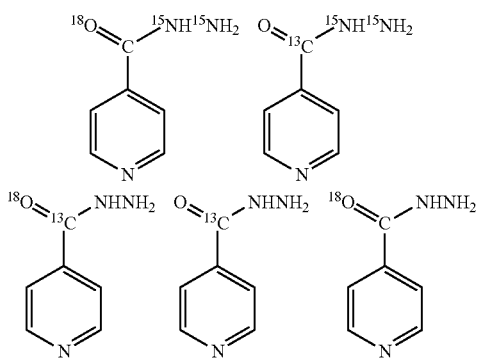

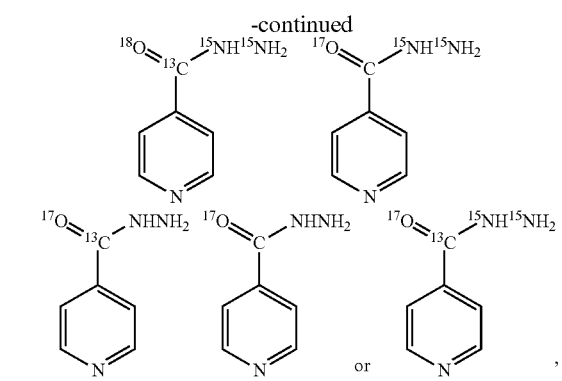

or a pharmaceutically acceptable salt thereof.

3. The compound according to claim 2 having an isotopically labeled oxygen-17 or oxygen-18 atom.

4. The compound according to claim 2 having an isotopically labeled carbon-13 atom.

5. The compound according to claim 2 having an isotopically labeled oxygen-17 atom.

6. The compound according to claim 2 having an isotopically labeled oxygen-18 atom.

7. The compound according to claim 2 having an isotopically labeled carbon-13 atom and an isotopically labeled oxygen-18 atom.

8. The compound according to claim 1 having an isotopically labeled nitrogen-15 atom.

9. A pharmaceutical composition in dosage form comprising a therapeutically effective amount of a compound according to claim 1 in an amount of at least 25 mg.

10. A pharmaceutical composition in dosage form comprising a therapeutically effective amount of a compound according to claim 1 in an amount of at least 50 mg.

11. A pharmaceutical composition in dosage form comprising a therapeutically effective amount of a compound according to claim 1 in an amount of at least 100 mg.

12. A pharmaceutical composition in dosage form comprising a therapeutically effective amount of a compound according to claim 1 in an amount of at least 150 mg.

13. A pharmaceutical composition in dosage form comprising a therapeutically effective amount of a compound according to claim 1 in an amount of at least 250 mg.

14. A pharmaceutical composition in dosage form comprising a therapeutically effective amount of a compound according to claim 1 in an amount of at least 300 mg.

15. The pharmaceutical composition according to claim 9 in oral dosage form.

16. The pharmaceutical composition according to claim 9 in parenteral dosage form.

17. The pharmaceutical composition according to claim 9 in pulmonary dosage form, 18. The pharmaceutical composition according to claim 10 in pulmonary dosage form.

19. The pharmaceutical composition according to claim 9 further comprising a therapeutically effective amount of at least one additional, anti-tuberculosis agent.

20. The pharmaceutical composition according to claim 19 wherein said anti-tuberculosis agent is selected from the group consisting of rifampin, pyrazinamide, ethambutol/ ethambutol hydrochloride, aminosalicyclic acid/aminosalicylate sodium, capreomycin sulfate, clofazimine, cycloserine, kanamycin sulfate, rifabutin, rifapentine, streptomycin sulfate, gatifloxacin and mixtures thereof.

21. The pharmaceutical composition according to claim 19 wherein said composition is a mixture of therapeutically effective amounts of isoniazid, rifampin, pyrazinamide and optionally, ethambutol/ethambutol hydrochloride.

22. The pharmaceutical composition according to claim 19 wherein said composition is a mixture of ethionamide and gatifloxacin, and optionally pyrazinamide all in therapeutically effective amounts.

23. The pharmaceutical composition according to claim 20 wherein said composition is a mixture of therapeutically effective amounts of isoniazid, rifampin, pyrazinamide and optionally, ethambutol/ethambutol hydrochloride.

24. The pharmaceutical composition according to claim 20 wherein said composition is a mixture of ethionamide and gatifloxacin, and optionally pyrazinamide all in therapeutically effective amounts.

25. A pharmaceutical composition in dosage form comprising a therapeutically effective amount of a compound according to claim 2 in an amount of at least 25 mg.

26. A pharmaceutical composition in dosage form comprising a therapeutically effective amount of a compound according to claim 2 in an amount of at least 100 mg.

* * * * *